(12) United States Patent
Rull Prous et al.

(10) Patent No.: US 11,819,528 B2
(45) Date of Patent: Nov. 21, 2023

(54) ENHANCED SOLUBILITY OF MILK THISTLE EXTRACT

(71) Applicant: EUROMED, S.A., Mollet del Valles (ES)

(72) Inventors: Santiago Rull Prous, Barcelona (ES); Anna Mula Daltell, Barcelona (ES); Agustin Villar Gonzalez, Ripollet (ES)

(73) Assignee: EUROMED, S.A., Mollet del Valles (ES)

( * ) Notice: Subject to any disclaimer, the term of this patent is extended or adjusted under 35 U.S.C. 154(b) by 0 days.

(21) Appl. No.: 16/137,415

(22) Filed: Sep. 20, 2018

(65) Prior Publication Data

US 2019/0091273 A1    Mar. 28, 2019

Related U.S. Application Data

(60) Provisional application No. 62/562,293, filed on Sep. 22, 2017.

(51) Int. Cl.
| | | |
|---|---|---|
| *A61K 36/00* | (2006.01) | |
| *A61K 36/28* | (2006.01) | |
| *A23L 33/105* | (2016.01) | |
| *A61K 9/00* | (2006.01) | |

(52) U.S. Cl.
CPC ............ *A61K 36/28* (2013.01); *A23L 33/105* (2016.08); *A61K 9/0053* (2013.01); *A61K 2236/00* (2013.01); *A61K 2236/17* (2013.01); *A61K 2236/333* (2013.01); *A61K 2236/51* (2013.01)

(58) Field of Classification Search
CPC .................................................. A61K 36/28
See application file for complete search history.

(56) References Cited

U.S. PATENT DOCUMENTS

| | | | | |
|---|---|---|---|---|
| 4,368,195 A * | 1/1983 | Madaus | ............... | C07D 407/04 424/764 |
| 2011/0027396 A1 | 2/2011 | Nagell et al. | | |
| 2012/0108825 A1 | 5/2012 | Rovati et al. | | |

FOREIGN PATENT DOCUMENTS

| | | | | |
|---|---|---|---|---|
| CN | 101925360 A | 12/2010 | | |
| CN | 103641821 A | 3/2014 | | |
| CN | 107595910 A | 1/2018 | | |
| CN | 107663200 A | 2/2018 | | |
| CN | 107663201 A | 2/2018 | | |
| CN | 107698572 A | 2/2018 | | |
| CZ | 20004404 A3 | 7/2002 | | |
| DE | 2914330 A1 | 10/1980 | | |
| DE | 3225688 A1 | 1/1984 | | |
| DE | 102008039271 A1 * | 6/2009 | ............. | A61P 35/00 |
| FR | 2181188 A5 | 11/1973 | | |
| KR | 20100126272 A | 12/2010 | | |
| RU | 2099076 C1 * | 12/1997 | | |
| WO | WO-0101961 A1 | 1/2001 | | |
| WO | WO-2013124700 A2 | 8/2013 | | |

OTHER PUBLICATIONS

Ahmad et al. "Milk Thistle" from Practical Handbook on Biodiesel Product and Properties. CRC Press: FL, 2013. p. 72. (Year: 2013).*
PCT/IB2018/001191 International Search Report and Written Opinion dated Mar. 7, 2019.
Shamama et al.: Reassessing Bioavailability of Silymarin. Alternative Medicine Review. 16(3):239-249 (2011).
Wallace et al.: Batch solvent extraction of flavanolignans from milk thistle. Phytochemical Analysis, J. Wiley. 16(1):7-16 (2005)Wallace et al.: Batch solvent extraction of flavanolignans from milk thistle. Phytochemical Analysis, J. Wiley. 16(1):7-16 (2005).
Yousaf et al.: Silymarin-laden PVP-PEG polymeric composite for enhanced aqueous solubility and dissolution rate: Preparaton and in vitro characterization. Journal of Pharmaceutical Analysis. 9:34-39 (2019).
Zhou et al.: Opening and closing of the periplasmic gate in lactose permease. PNAS. 105(10):3774-3778 (2008).

* cited by examiner

*Primary Examiner* — Qiuwen Mi
(74) *Attorney, Agent, or Firm* — Wilson Sonsini Goodrich & Rosati

(57) ABSTRACT

Described herein is a method for the production of a potent milk thistle extract. The method involves adding an oil to the milk thistle extract and results in an increase in the release rate of the plant drug. Also described herein is a product obtained by a method for the production of a potent milk thistle extract and the uses thereof.

18 Claims, 1 Drawing Sheet

Scanning electron microscope image of potent milk thistle extract
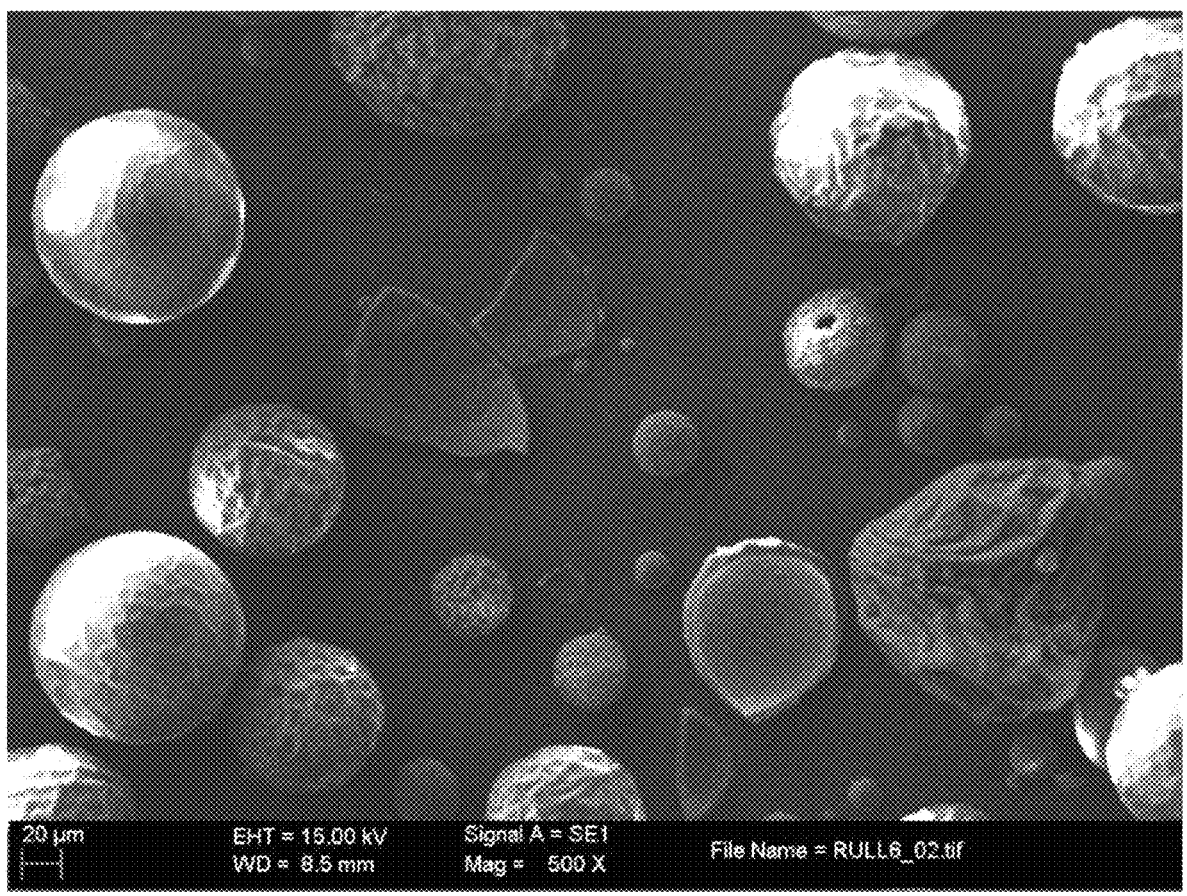

ENHANCED SOLUBILITY OF MILK THISTLE EXTRACT

CROSS-REFERENCE

This application claims the benefit of U.S. Provisional Application No. 62/562,293 filed Sep. 22, 2017, which application is incorporated herein by reference.

BACKGROUND OF THE INVENTION

The efficacy of the drug silymarin, extracted from milk thistle fruit, in the treatment and prevention of various forms of liver and gall bladder dysfunction is known. For general preparation of a milk thistle extract, the plant drug (silymarin) is extracted, purified and dried following the initial degreasing of the milk thistle fruit. It is known that the flavanolignans that comprise the plant drug have little or no solubility in water. This solubility characteristic hinders the release rate of these compounds and their bioavailability/absorbability into the body of humans or mammals is thus inadequate.

SUMMARY OF THE INVENTION

Disclosed herein is a potent milk thistle extract obtained by the following process:
- (a) providing an oily milk thistle extract obtained by degreasing the milk thistle fruit;
- (b) taking up the oily extract from (a) in an organic solvent to form a solution;
- (c) providing an additional extract from the degreased milk thistle fruit, wherein the additional extract is obtained by washing the degreased milk thistle fruit with a solvent and then subsequently removing said solvent;
- (d) taking up the additional extract from (c) in a solvent to form a solution;
- (e) combining the solution of (b), with the solution of (d) to form a combined extract solution, such that the amount of oily extract from (a) in the final product of (f) is 0.5-10.0% by weight;
- (f) removing the solvent of the combined extract solution of (e) to obtain a solid and optionally comminuting the solid;

wherein the product possesses a silymarin release rate is 90% or greater.

In one embodiment, the solution of (b) is concentrated and/or filtered. In one embodiment, the solution of (d) is concentrated and/or filtered. In one embodiment, the solution of (e) is concentrated and/or filtered. In one embodiment, the dried extract of (c) and/or (f) is comminuted. In one embodiment, the dried extract of (c) is re-solvated in an organic solvent, optionally concentrated and/or optionally filtered and dried and optionally comminuted prior to step (d). In one embodiment, the oily milk thistle extract of (a) is obtained by cold pressing of the milk thistle fruit. In one embodiment, the oily milk thistle extract of (a) is obtained by washing the milk thistle fruit with an organic solvent. In one embodiment, the solvent is a hydrocarbon solvent. In one embodiment, the oily milk thistle extract of (a) is obtained by extraction with supercritical gases or fluids. In one embodiment, the extraction is performed with supercritical carbon dioxide. In one embodiment, the obtained oily milk thistle extract of (a) is 5-35% by weight of the unprocessed milk thistle fruit, wherein the remaining 65-95% of weight is the degreased milk thistle fruit. In one embodiment, the solvent of (b) is an alcohol. In one embodiment, the solvent is ethanol. In one embodiment, the solvent of (c) is ethyl acetate, ethanol methanol, or acetone. In one embodiment, the solvent of (c) is ethyl acetate. In one embodiment, the solvent of claim (d) is an alcohol. In one embodiment, the solvent is ethanol. In one embodiment, the amount of oily extract in (e) is 0.5-6.0% by weight. In one embodiment, the amount of oily extract in (e) is 1-3% by weight. In one embodiment, the product has a release rate of silymarin of 91% or greater.

Disclosed herein is a milk thistle product comprising a milk thistle extract and an oil. In one embodiment, the milk thistle extract is obtained by washing a degreased milk thistle fruit with a solvent and then subsequently removing said solvent. In one embodiment, the degreased milk thistle fruit is obtained by cold pressing, thereby removing a milk thistle oil. In one embodiment, the oil is a plant oil, an animal oil, a petroleum oil, or any combinations thereof. In one embodiment, the oil is a vegetable oil, an essential oil, a herbal oil, or any combinations thereof. In one embodiment, the oil is a milk thistle oil. In one embodiment, the milk thistle oil is obtained by degreasing the milk thistle fruit. In one embodiment, the method of degreasing is cold pressing. In one embodiment, the milk thistle extract is obtained by washing the degreased milk thistle fruit with ethyl acetate, ethanol, or methanol, and then subsequently removing said solvent. In one embodiment, the product is obtained by combining milk thistle oil with the solvated milk thistle extract, and removing all solvents.

Disclosed herein is a pharmaceutical composition containing a therapeutically effective amount of a product of any processes disclosed herein. In one embodiment, the pharmaceutical composition comprises at least one pharmaceutically acceptable carrier. In one embodiment, the pharmaceutical composition is a tablet, dragee, capsule, pill, granule, suppository, solution, syrup, suspension, or emulsion.

Disclosed herein is a method for treating or preventing diseases of the liver, stomach or ball bladder in a subject by administering any of the products disclosed herein. In one embodiment, the liver disease is toxic liver damage, hepatoses, acute liver failure, liver necrosis, liver dystrophy, cirrhosis of the liver, hepatic fibrosis, hepatomegaly, fatty liver degeneration, liver insufficiency and hepatitis. In one embodiment, the liver disease is selected from the group consisting of fascioliasis, hepatitis, non-alcoholic steatohepatitis (NASH) with or without fibrosis, hepatic steatosis, fatty liver disease (FLD), non-alcoholic fatty liver disease (NAFLD), alcoholic liver disease, Alagille syndrome, biliary atresia, galactosemia, gallstones, hemochromatosis, liver cancer, lysosomal acid lipase deficiency (LALD), porphyria, acetaminophen hepatotoxicity, Reye's syndrome, sarcoidosis, tyrosinemia, Wilson disease, Gilbert's syndrome, cirrhosis and primary sclerosing cholangitis. In one embodiment, the hepatitis is hepatitis C. In one embodiment, the liver disease is non-alcoholic fatty liver disease.

Disclosed herein is a method for preparing milk thistle fruit extract having a silymarin release rate of 90% or greater, the method comprising:
- (a) providing an oily milk thistle extract obtained by degreasing the milk thistle fruit;
- (b) taking up the oily extract from (a) in an organic solvent to form a solution;
- (c) providing an additional extract from the degreased milk thistle fruit, wherein the additional extract is obtained by washing the degreased milk thistle fruit with a solvent and then subsequently removing said solvent;

(d) taking up the additional extract from (c) in an solvent to form a solution;

(e) combining the solution of (b), with the solution of (d) to form a combined extract solution, such that the amount of oily extract from (a) in the final product of (f) is 0.5-10.0% by weight;

(f) removing the solvent of the combined extract solution of (e) to obtain a solid and optionally comminuting the solid.

In one embodiment, the solution of (b) is concentrated and/or filtered. In one embodiment, the solution of (d) is concentrated and/or filtered. In one embodiment, the solution of (e) is concentrated and/or filtered. In one embodiment, the dried extract of (c) and/or (f) is comminuted. In one embodiment, the dried extract of (c) is re-solvated in an organic solvent, optionally concentrated and/or optionally filtered and dried and optionally comminuted prior to step (d). In one embodiment, the oily milk thistle extract of (a) is obtained by cold pressing of the milk thistle fruit. In one embodiment, the oily milk thistle extract of (a) is obtained by washing the milk thistle fruit with an organic solvent. In one embodiment, the solvent is a hydrocarbon solvent. In one embodiment, the oily milk thistle extract of (a) is obtained by extraction with or in combination with supercritical gases or fluids. In one embodiment, the extraction is performed with supercritical carbon dioxide. In one embodiment, the obtained oily milk thistle extract of (a) is 5-35% by weight of the unprocessed milk thistle fruit, wherein the remaining 65-95% of weight is the degreased milk thistle fruit. In one embodiment, the solvent of (b) is an alcohol. In one embodiment, the solvent is ethanol. In one embodiment, the solvent of (c) is ethyl acetate, ethanol or methanol. In one embodiment, the solvent of (c) is ethyl acetate. In one embodiment, the solvent of claim (d) is an alcohol. In one embodiment, the solvent is ethanol. In one embodiment, the amount of oily extract in (e) is 0.5-6.0% by weight. In one embodiment, the amount of oily extract in (e) is 1-3% by weight.

Disclosed herein is a product of any of the processes disclosed herein, wherein the product has a release rate of silymarin of 91% or greater.

Disclosed herein is a method for preparing an enhanced milk thistle extract comprising a milk thistle extract and an oil, wherein the addition of said oil to said milk thistle extract results in an increase in the silymarin release rate.

In one embodiment, the oil is derived from plant, animal or petrochemical sources. In one embodiment, the oil is derived from a plant. In one embodiment, the oil is derived from fruits, seeds or vegetables. In one embodiment, the oil is derived from milk thistle fruits and/or seeds. In one embodiment, the release rate is improved by 1.0% or more. In one embodiment, the release rate is improved by 5.0% or more. In one embodiment, the release rate is improved by 10.0% or more. In one embodiment, the release rate is improved by 20.0% or more.

BRIEF DESCRIPTION OF THE FIGURES

FIG. 1. shows a scanning electron microscope image of the potent milk thistle extract.

DETAILED DESCRIPTION OF THE INVENTION

In one embodiment, the present invention relates to a method for preparing a milk thistle fruit extract, in particular a flavanolignan preparation, having an increased release rate, and use thereof, in particular for the treatment and prevention of liver diseases. The disclosure also describes a product by the process of which it is made, given that the milk thistle extract described herein contains a mixture of naturally occurring chemical compounds, many of which are isomeric.

In one embodiment, the present disclosure provides a method for the production of a milk thistle fruit extract with an enhanced silymarin release rate. In some cases, the extract is prepared essentially without additives, supplements, carrier substances, or wetting agents. In one embodiment of the invention described herein, a method is given for preparing a milk thistle extract having a silymarin release rate of 90% or greater, using only components of the milk thistle fruit.

Generally, the preparation of a milk thistle fruit extract first requires the removal of an oily fraction within the milk thistle fruit. In some preparations, this oily fraction is discarded or used as an oil in an unrelated product, while the degreased milk thistle plant is washed with organic solvents to extract the silymarin drug. The washings are then processed to produce a solid extract.

In the invention disclosed herein, the oily fraction derived from the degreasing of the milk thistle fruit is re-added during the processing procedure of the solid extract. Unexpectedly, the addition of 0.5-10% by weight of the oil fraction to the extract produces a product with markedly superior dissolution characteristics. One would not expect that adding an oil to an extract whose principle components have low solubility would increase said solubility. The addition of an oil to another substance often imparts hydrophobic properties to the substance. One might also expect the addition of the oil to adversely affect the physical properties of the extract by enhancing the adhesiveness or decreasing the flowability of the extracted powder. However, no such observations have been made and the solid extract possesses excellent formulation properties.

In one embodiment of the invention, an oil may be added before, during or after the processing of the milk thistle extract to enhance the silymarin release rate of the extract. In some embodiments, the oil fraction is provided by the degreasing of the milk thistle fruit itself. In additional embodiments, the oil is provided from a source unrelated to the milk thistle fruit, such as a plant oil, an animal oil, a petroleum oil, or any combinations thereof. In some cases, the plant oil is a vegetable oil, an essential oil, a herbal supplement oil, or any combinations thereof.

Terms and Definitions

The term "solution" refers to both homogenous and/or heterogeneous mixtures of a material and a solvent.

The term "hydrocarbon solvent" refers to solvents that are constructed of hydrogen and carbon atoms. Examples of solvents include but are not limited to any solvent or mixture of solvents containing linear, branched or cyclic $C_5$-$C_{11}$ alkanes such as pentane, hexane, heptane, octane, nonane, decane, cyclopentane, cyclohexane, cycloheptane, cyclooctane, or $C_6$-$C_{10}$ aryls or arylalkanes such as benzene, toluene, xylene or ethyl benzene. The term may also apply to solvents that contain heteroatoms such as oxygen, nitrogen and fluorine that are not appreciably polar. Examples include but are not limited to diethyl ether, 1,4-dichlorobenzene and methyl t-butyl ether.

The term "supercritical gas or liquid" refers to a substance which is at a temperature or pressure above its critical point, where distinct liquid or gas phases do not exist. As such, the term "supercritical gas or liquid" is equivalent to "supercritical liquid" and "supercritical gas". Furthermore, the terms "supercritical liquid" and "supercritical gas" are used interchangeably and are meant to refer to the same physical state of matter. Examples of substance that may be used as supercritical gases or liquids include carbon dioxide, water, methane, ethane, butane, propane, ethylene, propene, butene, ethanol, methanol, propanol, nitrous oxide and dinitrogen.

The term "alcohol" preferably includes $C_1$-$C_4$ alcohols, particularly preferably ethanol, such as 99% or even 99.5% pure.

Within the scope of the present disclosure, "silymarin" refers to a substance mixture containing (at least) the four substances silibinin, silidianin, silicristin, and isosilbinin in various concentrations.

A "silymarin release rate of 90% or greater" means that the active substances are at least 90% soluble in aqueous solution.

The term "oil" describes an unctuous, combustible substance which is liquid, or easily liquefiable, on warming, and is soluble in ether but insoluble in water. Oils may be described as animal, plant or petrochemical, depending on their origin. The term also includes long chain fatty acids, esters, alcohols, or alkanes. The term additionally includes silicones, hydrocarbons, glucosides, glutamates, glycerides, glyceryl esters and waxes.

The term "dietary supplement" refers to a product that supplements the diet. A dietary supplement is distinct from a drug which must undergo extensive testing and be preapproved by the FDA before being sold. In some cases, dietary supplements may be labeled as impacting a disease or condition. Dietary supplements are not represented for use as a conventional food or as the sole item of a meal or diet. Dietary supplements are typically adapted to supplement, i.e., add to, an individual's dietary intake of one or more dietary components The term "potent milk thistle extract" describes a milk thistle extract obtained by a process in which an oil has been added and also possesses an enhanced release rate or dissolution rate as compared to a milk thistle extract obtained by a process not comprising the step of adding an oil.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "optional" or "optionally" means that the subsequently described event or circumstance may or may not occur, and that the description includes instances where said event or circumstance occurs and instances in which it does not.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, PA, 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, FL, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Method of Preparation and Product by Process

Described herein are methods for preparing a milk thistle fruit extract comprising:
  (a) providing an oily milk thistle extract obtained by degreasing the milk thistle fruit;
  (b) taking up the oily extract from (a) in an organic solvent to form a solution;
  (c) providing an additional extract from the degreased milk thistle fruit, wherein the additional extract is obtained by washing the degreased milk thistle fruit with a solvent and then subsequently removing said solvent;
  (d) taking up the additional extract from (c) in a solvent to form a solution;
  (e) combining a portion of the solution of (b), with the solution of (d) to form a combined extract solution, such that the amount of oily extract from (a) in the final product of (f) is 0.5-10.0% by weight;
  (f) removing the solvent of the combined extract solution of (e) to obtain a solid and optionally comminuting the solid, wherein the product possesses a silymarin release rate is 90% or greater.

In one embodiment disclosed herein is a method for preparing milk thistle extract, wherein the addition of an oil to a milk thistle extract results in an increase in the silymarin release rate. In some embodiments, the addition of an oil to the milk thistle extract produces a 1% or greater increase in the silymarin release rate. In some embodiments, the addition of an oil to the milk thistle extract produces a 2% or greater increase in the silymarin release rate. In some embodiments, the addition of an oil to the milk thistle extract produces a 5% or greater increase in the silymarin release rate. In some embodiments, the addition of an oil to the milk thistle extract produces a 10% or greater increase in the silymarin release rate. In some embodiments, the addition of an oil to the milk thistle extract produces a 15% or greater increase in the silymarin release rate. In some embodiments, the addition of an oil to the milk thistle extract produces a 20% or greater increase in the silymarin release rate. In some embodiments, the addition of an oil to the milk thistle extract produces a 30% or greater increase in the silymarin release rate. In some embodiments, the addition of an oil to the milk thistle extract produces a 50% or greater increase in the silymarin release rate.

In another embodiment disclosed herein is a product that exhibits an enhanced silymarin release rate. In some embodiments, the product is produced from a process comprising the step of adding an oil. The product is compared to the product obtained by a process not comprising the step of adding an oil. In some embodiments, the addition of an oil to the milk thistle extract produces a 1% or greater increase in the silymarin release rate. In some embodiments, the addition of an oil to the milk thistle extract produces a 2% or greater increase in the silymarin release rate. In some embodiments, the addition of an oil to the milk thistle extract produces a 5% or greater increase in the silymarin release rate. In some embodiments, the addition of an oil to the milk thistle extract produces a 10% or greater increase in the silymarin release rate. In some embodiments, the addition of an oil to the milk thistle extract produces a 15% or greater increase in the silymarin release rate. In some embodiments, the addition of an oil to the milk thistle extract produces a 20% or greater increase in the silymarin release rate. In some embodiments, the addition of an oil to the milk thistle extract produces a 30% or greater increase in the silymarin release rate. In some embodiments, the addition of an oil to the milk thistle extract produces a 50% or greater increase in the silymarin release rate.

Also disclosed herein is a potent milk thistle extract produced by the following process:
(a) providing an oily milk thistle extract obtained by degreasing the milk thistle fruit;
(b) taking up the oily extract from (a) in an organic solvent to form a solution;
(c) providing an additional extract from the degreased milk thistle fruit, wherein the additional extract is obtained by washing the degreased milk thistle fruit with a solvent and then subsequently removing said solvent;
(d) taking up the additional extract from (c) in a solvent to form a solution;
(e) combining the solution of (b), with the solution of (d) to form a combined extract solution, such that the amount of oily extract from (a) in the final product of (f) is 0.5-10.0% by weight;
(f) removing the solvent of the combined extract solution of (e) to obtain a solid and optionally comminuting the solid, wherein the product possesses a silymarin release rate is 90% or greater.

In some embodiments, the solution of (b) is concentrated and/or filtered. In some embodiments, the solution of (d) is concentrated and/or filtered. In some embodiments, the solution of (e) is concentrated and/or filtered. In some embodiments, the dried extract of (c) and/or (f) is comminuted. In some embodiments, the dried extract of (c) is re-solvated in an organic solvent, optionally concentrated and/or optionally filtered, and dried to provide a solid, of which is optionally comminuted prior to step (d).

In some embodiments, the oily milk thistle extract of (a) is obtained by cold pressing of the milk thistle fruit. In some embodiments, the oily milk thistle extract of (a) is obtained by washing the milk thistle fruit with an organic solvent.

In some embodiments, the solvent of (a) is a hydrocarbon solvent. In some embodiments, the oily milk thistle extract of (a) is obtained by extraction with or in combination with supercritical gases or fluids. In some embodiments, the extraction is performed with supercritical carbon dioxide. In some embodiments, the solvent of (b) is an alcohol. In some embodiments, the solvent of (b) is ethanol. In some embodiments, the solvent of (c) is ethyl acetate, ethanol, methanol or acetone. In some embodiments, the solvent of (c) is ethyl acetate. In some embodiments, the solvent of claim (d) is an alcohol. In some embodiments, the solvent is ethanol.

In some embodiments, the amount of oily extract in (e) is 0.5-6.0% by weight. In some embodiments, the amount of oily extract in (e) is 1-3% by weight.

In another embodiment, the method for preparing a milk thistle fruit extract is described in a method comprising:
(a) The plant fruit is degreased by either mechanical cold pressing or by washing with hydrocarbon solvents or supercritical fluids. In the case where hydrocarbon solvents are used, the solvent is subsequently removed. In some cases, the oily fraction is filtered or concentrated. The oily fraction isolated is typically between 5-35% by weight of the unprocessed milk thistle fruit. The degreased milk thistle fruit contains the remainder of the weight.
(b) The oily fraction from (a) is combined with an organic solvent to form a solution, non-limiting examples of which include ethanol, propanol, diethylether, hexane and ethyl acetate. This solution is optionally concentrated and/or filtered.
(c) The degreased milk thistle fruit is washed with an organic solvent, non-limiting examples of which include ethyl acetate, ethanol, acetone and methanol. The resulting solution optionally contains aqueous fractions. The solution is optionally washed with hexane or another non-polar solvent. The solution is also optionally concentrated and/or filtered. The solution is dried, optionally under vacuum with stirring. The resulting raw extract is optionally washed with hot water and dried, and/or optionally comminuted.
(d) The raw extract obtained in (c) is re-dissolved in an organic solvent, non-limiting examples of which include alcohols such as methanol, ethanol, propanol and butanol. The resulting solution is optionally concentrated and/or filtered.
(e) The solution of (d) is combined with the solution of (b), in a ratio such that the final product of step (f) contains 0.5-10.0% by weight of the oily fraction obtained in (a). The solution is optionally concentrated and/or filtered.
(f) removing the solvent of the combined extract solution of (e) to obtain a solid and optionally comminuting the solid, wherein the product possesses a silymarin release rate is 90% or greater.

In another embodiment, a potent milk thistle extract is produced by the process comprising:
(a) The plant fruit is degreased by either mechanical cold pressing or by washing with hydrocarbon solvents or supercritical fluids. In the case where hydrocarbon solvents are used, the solvent is subsequently removed. In some cases, the oily fraction is filtered or concentrated. The oily fraction isolated is typically between 5-35% by weight of the unprocessed milk thistle fruit. The degreased milk thistle fruit contains the remainder of the weight.
(b) The oily fraction from (a) is combined with an organic solvent to form a solution, non-limiting examples of which include ethanol, propanol, diethylether, hexane and ethyl acetate. This solution is optionally concentrated and/or filtered.
(c) The degreased milk thistle fruit is washed with an organic solvent, non-limiting examples of which include ethyl acetate, ethanol, acetone and methanol. The resulting solution optionally contains aqueous fractions. The solution is optionally washed with hexane or another non-polar solvent. The solution is also optionally concentrated and/or filtered. The solution is dried, optionally under vacuum with stirring. The resulting raw extract is optionally washed with hot water and dried, and/or optionally comminuted.
(d) The raw extract obtained in (c) is re-dissolved in an organic solvent, non-limiting examples of which include alcohols such as methanol, ethanol, propanol and butanol. The resulting solution is optionally concentrated and/or filtered.
(e) The solution of (d) is combined with the solution of (b), in a ratio such that the final product of step (f) contains 0.5-10.0% by weight of the oily fraction obtained in (a). The solution is optionally concentrated and/or filtered.
(f) removing the solvent of the combined extract solution of (e) to obtain a solid and optionally comminuting the solid, wherein the product possesses a silymarin release rate is 90% or greater.

In some embodiments, the extraction of step (c) is performed at 40-80 degrees Celsius. In another embodiment, the extraction is performed at 50-70 degrees Celsius.

In some embodiments, the solution of step (c) is dried at a temperature of less than 60 degrees Celsius. In another embodiment, the solution is dried at a temperature of less than 40 degrees Celsius.

In some embodiments, the ethanol used in step (d) is 96% ethanol or greater. In some embodiments, the combined solutions are concentrated at a pressure of 1-100 mbar.

In one embodiment, the method for preparing a milk thistle fruit extract is described in a method comprising:
(a) providing an oily milk thistle obtained by cold pressing the milk thistle fruit;
(b) taking up the oily extract from (a) in ethanol to form a solution;
(c) providing an additional extract from the degreased milk thistle fruit, wherein the additional extract is obtained by washing the degreased milk thistle fruit with ethyl acetate and then subsequently removing said solvent;
(d) taking up the additional extract from (c) in an ethanol to form a solution;
(e) combining the solution of (b), with the solution of (d) to form a combined extract solution, such that the amount of oily extract from (a) in the final product of (f) is 1.0-3.0% by weight;
(f) removing the solvent of the combined extract solution of (e) to obtain a solid and optionally comminuting the solid, wherein the product possesses a silymarin release rate is 90% or greater.

In one embodiment, a potent milk thistle extract is produced by the following process comprising:
(a) providing an oily milk thistle obtained by cold pressing the milk thistle fruit;
(b) taking up the oily extract from (a) in ethanol to form a solution;
(c) providing an additional extract from the degreased milk thistle fruit, wherein the additional extract is obtained by washing the degreased milk thistle fruit with ethyl acetate and then subsequently removing said solvent;
(d) taking up the additional extract from (c) in an ethanol to form a solution;
(e) combining the solution of (b), with the solution of (d) to form a combined extract solution, such that the amount of oily extract from (a) in the final product of (f) is 1.0-3.0% by weight;
(f) removing the solvent of the combined extract solution of (e) to obtain a solid and optionally comminuting the solid, wherein the product possesses a silymarin release rate is 90% or greater.

In some embodiments of the disclosure, the silymarin release rate of the milk thistle extract is 85% or greater. In some embodiments, the silymarin release rate is 90% or greater. In some embodiments, the silymarin release rate is 91% or greater.

In some embodiments, a supercritical gas and/or fluid is used to degrease the milk thistle fruit in step (a). In some cases, the milk thistle fruit is chopped, milled, grinded or otherwise comminuted into a paste. The paste can be stirred or agitated in the presence of the supercritical fluid to facilitate degreasing. In some embodiments, carbon dioxide is the supercritical gas in the degreasing process. In other embodiments, non-limiting examples of supercritical gases or fluids include methane, ethane, butane, propane, ethylene, propene, butene, ethanol, methanol, propanol, water, nitrous oxide and dinitrogen.

In some embodiments, hydrocarbon solvents are used to degrease the milk thistle fruit. In some cases, the milk thistle fruit is chopped, milled, grinded or otherwise comminuted into a paste. The paste can be stirred or agitated in the presence of the hydrocarbon solvent to facilitate degreasing. Hydrocarbon solvents include linear, branched or cyclic $C_5$-$C_{11}$ alkanes such as pentane, hexane, heptane, octane, nonane, decane, cyclopentane, cyclohexane, cycloheptane, cyclooctane, or $C_6$-$C_{10}$ aryls or arylalkanes such as benzene, toluene, xylene or ethyl benzene. In some embodiments, said hydrocarbon solvents contain heteroatoms such as oxygen, nitrogen and fluorine wherein the molecule is not appreciably polar, or has a dipole moment below 2. In some embodiments, the dipole moment is below 1.5. Examples include but are not limited to diethyl ether, 1,4-dichlorobenzene and methyl t-butyl ether.

In some embodiments, the extraction of the oily fraction is obtained by means of cold pressing. In some embodiments, the process of cold pressing involves chopping, grinding, milling or comminuting the raw milk thistle fruit. This results in the formation of a semi-solid paste. The material is then be mechanically pressed to force the oily fraction away from the solid material. In some embodiments, the fraction passes through a filter or filters. In some embodiments, no external heat is applied to the process during milling, pressing or filtering.

In some embodiments, the oily fraction obtained by the cold pressing of milk thistle fruit is re-added to the extract obtained by washing the degreased milk thistle fruit. The re-addition of the milk thistle oil to the extract increases the release rate of silymarin in the final product. In alternate embodiments, a plant oil other than milk thistle oil is added to increase the release rate of silymarin. Disclosed herein are non-limiting examples of plant derived oils to be utilized as additives such as coconut oil, corn oil, cottonseed oil, olive oil, palm oil, peanut oil, rapeseed oil, canola oil, safflower oil, sesame oil, soybean oil, sunflower oil, almond oil, beech nut oil, brazil nut oil, cashew oil, hazelnut oil, macadamia oil, mongongo nut oil, pecan oil, pine nut oil, pistachio oil, walnut oil, grapefruit seed oil, lemon oil, orange oil, bitter gourd oil, buffalo gourd oil, butternut squash seed oil, pumpkin seed oil, watermelon seed oil, açaí oil, black seed oil, blackcurrant seed oil, borage seed oil, flaxseed oil, amaranth oil, apricot oil, apple seed oil, argan oil, avocado oil, babassu oil, ben oil, borneo tallow nut oil, carob pod oil (algaroba oil), cocoa butter sometimes known as theobroma oil, cocklebur oil, sunflower oil, cohune oil, coriander seed oil, date seed oil, dika oil, false flax oil, grape seed oil, hemp oil, kapok seed oil, kenaf seed oil, cottonseed oil, lallemantia oil, mafura oil, marula oil, meadowfoam seed oil, mustard oil, niger seed oil, nutmeg oil, okra seed oil, perilla seed oil, persimmon seed oil, pequi oil, pili nut oil, pomegranate seed oil, poppyseed oil, pracaxi oil, prune kernel oil, quinoa oil, ramtil oil, rice bran oil, royle oil, sacha inchi oil, sapote oil, seje oil, shea oil, taramira oil, tea seed oil, tigernut oil (or nut-sedge oil), tobacco seed oil, tomato seed oil, wheat germ oil, agar oil, ajwain oil, angelica root oil, anise oil, asafoetida oil, basil oil, bay oil, bergamot oil, black pepper oil, buchu oil, birch oil, camphor oil, cannabis flower essential oil, calamodin oil, calamansi essential oil, caraway oil, cardamom seed oil, carrot seed oil, cedar oil (or cedarwood oil), chamomile oil, calamus oil, cinnamon oil, citron oil, citronella oil, clary sage oil, coconut oil, coffee oil, coriander oil, costmary oil (bible leaf oil), costus root oil, cranberry seed oil, cubeb oil, cumin oil, cypress oil, cypriol oil, curry leaf oil, davana oil, elecampane oil, elemi oil, eucalyptus oil, fennel seed oil, fenugreek oil, fir oil, frankincense oil, galangal oil, galbanum oil, geranium oil, ginger oil, goldenrod oil, helichrysum oil, hickory nut oil, horseradish oil, jasmine oil, juniper berry oil, lavender oil, melaleuca see tea tree oil, melissa oil, mint oil, moringa oil, mugwort oil, myrrh oil, myrtle neem oil or neem tree oil, oregano oil, orris oil, parsley oil, patchouli oil, perilla essential oil, pennyroyal oil, peppermint oil, pine oil, rose oil, rosehip oil, rosemary oil, rosewood oil, sage oil, sassafras oil, savory oil, saw palmetto oil, schisandra oil, spearmint oil, spruce oil, star anise oil, tarragon oil, tea tree oil, thyme oil, vetiver oil (khus oil) and yarrow oil.

In some embodiments, examples of animal derived oils for use in the disclosed method include but are not limited to bone oil, cod liver oil, fish oil, goose grease, halibut-liver oil, lard oil, menhaden oil, neat's-foot oil, oleo oil, salmon oil, sardine oil, shark oil, wool oil and tallow oil. In some embodiments, examples of petrochemical derived oils for use in the disclosed method include but are not limited to mineral oil, silicone oil, petroleum jelly and mixtures of $C_{9-20}$ alkanes.

In some embodiments, the requirements for a dry extract are a content of preferably 35-70% by weight silymarin, the silymarin portion containing the following fractions of 40-65% by weight: silibinin A and B (diastereomeric mixture, $C_{25}H_{22}O_{10}$, MW 482.4); 10-20% by weight isosilibinin A and B (diastereomeric mixture, $C_{25}H_{22}O_{10}$, MW 482.4); and 20-45% by weight: ailidanin and silicristin ($C_{25}H_{22}O_{10}$, MW 482.4).

Use and Pharmaceutical Compositions

Also disclosed herein is a pharmaceutical formulation comprising an effective amount of the milk thistle fruit extract disclosed herein.

In some embodiments, the pharmaceutical formulation comprising the milk thistle fruit extract disclosed herein is used for treatment and prevention of liver and gall bladder dysfunction, in particular for toxic liver damage (fatty liver, alcohol), hepatoses such as mushroom poisoning, acute liver failure, liver necrosis, liver dystrophy, liver disease, cirrhosis of the liver, hepatic fibrosis, hepatomegaly, and fatty liver degeneration, liver insufficiency, and hepatitis, in particular hepatitis C.

In some embodiments, the pharmaceutical formulation comprising the milk thistle fruit extract disclosed herein is used for treatment and prevention of liver diseases such as fascioliasis, hepatitis, non-alcoholic steatohepatitis (NASH) with or without fibrosis, hepatic steatosis, fatty liver disease (FLD), non-alcoholic fatty liver disease (NAFLD), alcoholic liver disease, Alagille syndrome, biliary atresia, galactosemia, gallstones, hemochromatosis, liver cancer, lysosomal acid lipase deficiency (LALD), porphyria, acetaminophen hepatotoxicity, Reye's syndrome, sarcoidosis, tyrosinemia, Wilson disease, Gilbert's syndrome, cirrhosis and primary sclerosing cholangitis.

The milk thistle fruit extracts disclosed herein may be provided in the form of pharmaceutical preparations in dosage units. In some embodiments, the preparation is present in the form of individual portions, for example tablets, dragees, capsules, pills, suppositories, and ampoules, the active substance content of which optionally corresponds to a fraction or a multiple of a single dose. The dosage units may contain, for example, 1, 2, 3, or 4 single doses. A single dose preferably contains the quantity of active substance which is dispensed in one administration, and which typically corresponds to a whole daily dose or a half, third, or fourth of a daily dose.

Nontoxic, inert, pharmaceutically suitable carrier substances are understood to mean solid, semisolid, or liquid diluents, fillers, and formulation adjuvants of all types.

Tablets, dragees, capsules, pills, granules, suppositories, solutions, syrups, suspensions, and emulsions are named as preferred pharmaceutical formulations. Tablets, dragees, capsules, pills, and granules may contain the active substance or substances in addition to the customary carrier substances, such as a) fillers and extenders, for example starches, lactose, sucrose, glucose, mannite, and silicic acid, b) binders, for example carboxymethylcellulose, alginates, gelatins, and polyvinylpyrrolidone, c) humectants, for example glycerin, d) disintegrants, for example agar-agar, calcium carbonate, and sodium carbonate, e) solubility retardants, for example paraffin, f) absorption accelerators, for example quaternary ammonium compounds, g) wetting agents, for example cetyl alcohol and glycerin mono stearate, h) adsorbents, for example kaolin and bentonite, and i) lubricants, for example talc, calcium and magnesium stearate, and solid polyethylene glycols, or mixtures of the substances stated under a) through i).

Tablets, dragees, capsules, pills, and granules may be provided with customary coatings and shells optionally containing opacifying agents, and may also have a composition such that they deliver the active substance or substances only in the intestinal tract or preferably in a specific portion thereof, optionally in a delayed manner, wherein polymeric substances and waxes, for example, may be used as encapsulating compounds.

The active substance or substances may also be present in microencapsulated form, optionally with one or more of the above-referenced carrier substances.

In addition to the active substance or substances, suppositories may contain customary water-soluble or water insoluble carrier substances, for example polyethylene glycols, fats, for example cocoa butter, and higher esters (for example, $C_{14}$ alcohol with $C_{16}$ fatty acid), or mixtures of these substances.

In addition to the active substance or substances, solutions and emulsions may contain customary carrier substances such as solvents, solubilizers, and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, peanut oil, corn germ oil, olive oil, castor oil, and sesame oil, glycerin, glycerin formal, tetrahydrofurfuryl alcohol, polyethylene glycols, and fatty acid esters of sorbitan, or mixtures of these substances.

In addition to the active substance or substances, suspensions may contain customary carrier substances such as liquid diluents, for example water, ethyl alcohol, and propylene glycol, suspension agents, for example ethoxylated isostearyl alcohols, polyoxyethylene sorbite, and sorbitan esters, microcrystalline cellulose, aluminum metahydroxide, bentonite, agar-agar, and gum tragacanth, or mixtures of these substances. The referenced formulation forms may also contain dyes, preservatives, and fragrance- and taste-enhancing additives, for example peppermint oil and eucalyptus oil, and sweeteners, for example saccharin.

Disclosed herein is a dietary supplement composition containing the product of any one of the processes described within. In some embodiments, the dietary supplement composition is a tablet, dragee, capsule, pill, granule, solution, syrup, suspension or emulsion. In some embodiments, the dietary supplement composition is for use in modifying liver function. In some embodiments, the dietary supplement composition is used for treatment and prevention of liver diseases such as fascioliasis, hepatitis, non-alcoholic steatohepatitis (NASH) with or without fibrosis, hepatic steatosis, fatty liver disease (FLD), non-alcoholic fatty liver disease (NAFLD), alcoholic liver disease, Alagille syndrome, biliary atresia, galactosemia, gallstones, hemochromatosis, liver cancer, lysosomal acid lipase deficiency (LALD), porphyria, acetaminophen hepatotoxicity, Reye's syndrome, sarcoidosis, tyrosinemia, Wilson disease, Gilbert's syndrome, cirrhosis and primary sclerosing cholangitis.

Additional Embodiments

Embodiment 1: disclosed herein is a potent milk thistle extract obtained by the following process:
(a) providing an oily milk thistle extract obtained by degreasing the milk thistle fruit;
(b) taking up the oily extract from (a) in an organic solvent to form a solution;
(c) providing an additional extract from the degreased milk thistle fruit, wherein
the additional extract is obtained by washing the degreased milk thistle fruit with a solvent and then
subsequently removing said solvent;
(d) taking up the additional extract from (c) in a solvent to form a solution;
(e) combining the solution of (b), with the solution of (d) to form a combined
extract solution, such that the amount of oily extract from (a) in the final product of (f) is 0.5-10.0%
by weight;
(f) removing the solvent of the combined extract solution of (e) to obtain a solid and optionally comminuting the solid;
wherein the product possesses a silymarin release rate is 90% or greater.

Embodiment 2: the product of embodiment 1, wherein the solution of (b) is concentrated and/or filtered.

Embodiment 3: the product of embodiment 1 or 2, wherein the solution of (d) is concentrated and/or filtered.

Embodiment 4: the product of any of embodiments 1-3, wherein the solution of (e) is concentrated and/or filtered.

Embodiment 5: the product of any of embodiments 1-4, wherein the dried extract of (c) and/or (f) is comminuted.

Embodiment 6: the product of any of embodiments 1-5, wherein the dried extract of (c) is re-solvated in an organic solvent, optionally concentrated and/or optionally filtered and dried and optionally comminuted prior to step (d).

Embodiment 7: the product of any of embodiments 1-6, wherein the oily milk thistle extract of (a) is obtained by cold pressing of the milk thistle fruit.

Embodiment 8: the product of any of embodiments 1-6, wherein the oily milk thistle extract of (a) is obtained by washing the milk thistle fruit with an organic solvent.

Embodiment 9: the product of embodiment 8 wherein the solvent is a hydrocarbon solvent.

Embodiment 10: the product of any of embodiments 1-6, wherein the oily milk thistle extract of (a) is obtained by extraction with supercritical gases or fluids.

Embodiment 11: the product of embodiment 10 wherein the extraction is performed with supercritical carbon dioxide.

Embodiment 12: the product of any of embodiments 1-11, wherein the obtained oily milk thistle extract of (a) is 5-35% by weight of the unprocessed milk thistle fruit, wherein the remaining 65-95% of weight is the degreased milk thistle fruit.

Embodiment 13: the product of any of embodiments 1-12, wherein the solvent of (b) is an alcohol.

Embodiment 14: the product embodiment 13, wherein the solvent is ethanol.

Embodiment 15: the product of any of embodiments 1-14, wherein the solvent of (c) is ethyl acetate, ethanol methanol, or acetone.

Embodiment 16: the product of embodiment 15, wherein the solvent of (c) is ethyl acetate.

Embodiment 17: the product of any of embodiments 1-16, wherein the solvent of embodiment (d) is an alcohol.

Embodiment 18: the product of embodiment 17, wherein the solvent is ethanol.

Embodiment 19: the product of any of embodiments 1-18, wherein the amount of oily extract in (e) is 0.5-6.0% by weight.

Embodiment 20: the product of embodiment 19, wherein the amount of oily extract in (e) is 1-3% by weight.

Embodiment 21: the product of any of embodiments 1-20, wherein the product has a release rate of silymarin of 91% or greater.

Embodiment 22: disclosed herein is a milk thistle product comprising a milk thistle extract and an oil.

Embodiment 23: the milk thistle product of embodiment 22, wherein the milk thistle extract is obtained by washing a degreased milk thistle fruit with a solvent and then subsequently removing said solvent.

Embodiment 24: the milk thistle product of embodiments 22 or 23, wherein the degreased milk thistle fruit is obtained by cold pressing, thereby removing a milk thistle oil.

Embodiment 25: the milk thistle product of any of embodiments 22-24, wherein the oil is a plant oil, an animal oil, a petroleum oil, or any combinations thereof.

Embodiment 26: the milk thistle product of any of embodiments 22-25, wherein the oil is a vegetable oil, an essential oil, a herbal oil, or any combinations thereof.

Embodiment 27: the milk thistle product of any of embodiments 22-26, wherein the oil is a milk thistle oil.

Embodiment 28: the milk thistle product of embodiment any of embodiments 22-27 wherein the milk thistle oil is obtained by degreasing the milk thistle fruit.

Embodiment 29: the milk thistle product of embodiment any of embodiments 22-28, wherein the method of degreasing is cold pressing.

Embodiment 30: the milk thistle product of embodiment any of embodiments 22-29, wherein the milk thistle extract is obtained by washing the degreased milk thistle fruit with ethyl acetate, ethanol, or methanol, and then subsequently removing said solvent.

Embodiment 31: the milk thistle product of embodiment any of embodiments 22-30, wherein the product is obtained by combining milk thistle oil with the solvated milk thistle extract, and removing all solvents.

Embodiment 32: disclosed herein is a pharmaceutical composition containing a therapeutically effective amount of a product of any of embodiments 1-31.

Embodiment 33: the pharmaceutical composition of embodiment 32 and at least one pharmaceutically acceptable carrier.

Embodiment 34: the pharmaceutical composition of embodiment 32 wherein the pharmaceutical composition is a tablet, dragee, capsule, pill, granule, suppository, solution, syrup, suspension, or emulsion.

Embodiment 35: disclosed herein is a method for treating or preventing diseases of the liver, stomach or ball bladder in a subject by administering a product of any of embodiments 1-31.

Embodiment 36: the method for treating or preventing liver disease according to embodiment 35, wherein the liver disease is toxic liver damage, hepatoses, acute liver failure, liver necrosis, liver dystrophy, cirrhosis of the liver, hepatic fibrosis, hepatomegaly, fatty liver degeneration, liver insufficiency and hepatitis.

Embodiment 37: the method of embodiment 35, wherein the liver disease is selected from the group consisting of fascioliasis, hepatitis, non-alcoholic steatohepatitis (NASH) with or without fibrosis, hepatic steatosis, fatty liver disease (FLD), non-alcoholic fatty liver disease (NAFLD), alcoholic liver disease, Alagille syndrome, biliary atresia, galactosemia, gallstones, hemochromatosis, liver cancer, lysosomal acid lipase deficiency (LALD), porphyria, acetaminophen hepatotoxicity, Reye's syndrome, sarcoidosis, tyrosinemia, Wilson disease, Gilbert's syndrome, cirrhosis and primary sclerosing cholangitis.

Embodiment 38: the method of embodiment 36, wherein the hepatitis is hepatitis C.

Embodiment 39: the method of embodiment 37, wherein liver disease is non-alcoholic fatty liver disease.

Embodiment 40: disclosed herein is a method for preparing milk thistle fruit extract having a silymarin release rate of 90% or greater, the method comprising:
(a) providing an oily milk thistle extract obtained by degreasing the milk thistle fruit;
(b) taking up the oily extract from (a) in an organic solvent to form a solution;
(c) providing an additional extract from the degreased milk thistle fruit, wherein
the additional extract is obtained by washing the degreased milk thistle fruit with a solvent and then subsequently removing said solvent;
(d) taking up the additional extract from (c) in an solvent to form a solution;
(e) combining the solution of (b), with the solution of (d) to form a combined
extract solution, such that the amount of oily extract from (a) in the final product of (f) is 0.5-10.0% by weight;
(f) removing the solvent of the combined extract solution of (e) to obtain a solid and optionally comminuting the solid.

Embodiment 41: the method of embodiment 40, wherein the solution of (b) is concentrated and/or filtered.

Embodiment 42: the method of embodiment 40 or 41, wherein the solution of (d) is concentrated and/or filtered.

Embodiment 43: the method of any of embodiments 40-42, wherein the solution of (e) is concentrated and/or filtered.

Embodiment 44: the method of any of embodiments 40-43, wherein the dried extract of (c) and/or (f) is comminuted.

Embodiment 45: the method of any of embodiments 40-44, wherein the dried extract of (c) is re-solvated in an organic solvent, optionally concentrated and/or optionally filtered and dried and optionally comminuted prior to step (d).

Embodiment 46: the method of any of embodiments 40-45, wherein the oily milk thistle extract of (a) is obtained by cold pressing of the milk thistle fruit.

Embodiment 47: the method of any of embodiments 40-45, wherein the oily milk thistle extract of (a) is obtained by washing the milk thistle fruit with an organic solvent.

Embodiment 48: the method of embodiment 47 wherein the solvent is a hydrocarbon solvent.

Embodiment 49: the method of any of embodiments 40-45, wherein the oily milk thistle extract of (a) is obtained by extraction with or in combination with supercritical gases or fluids.

Embodiment 50: the method of embodiment 49 wherein the extraction is performed with supercritical carbon dioxide.

Embodiment 51: the method of any of embodiments 40-50, wherein the obtained oily milk thistle extract of (a) is 5-35% by weight of the unprocessed milk thistle fruit, wherein the remaining 65-95% of weight is the degreased milk thistle fruit.

Embodiment 52: the method of any of embodiments 40-51, wherein the solvent of (b) is an alcohol.

Embodiment 53: the method embodiment 52, wherein the solvent is ethanol.

Embodiment 54: the method of any of embodiments 40-53, wherein the solvent of (c) is ethyl acetate, ethanol or methanol.

Embodiment 55: the method of embodiment 54, wherein the solvent of (c) is ethyl acetate.

Embodiment 56: the method of any of embodiments 40-55, wherein the solvent of embodiment (d) is an alcohol.

Embodiment 57: the method of embodiment 56, wherein the solvent is ethanol.

Embodiment 58: the method of any of embodiments 40-57, wherein the amount of oily extract in (e) is 0.5-6.0% by weight.

Embodiment 59: the method of embodiment 58, wherein the amount of oily extract in (e) is 1-3% by weight.

Embodiment 60: disclosed herein is a product of any of embodiments 40-59, wherein the product has a release rate of silymarin of 91% or greater.

Embodiment 61: disclosed herein is a method for preparing an enhanced milk thistle extract comprising a milk thistle extract and an oil, wherein the addition of said oil to said milk thistle extract results in an increase in the silymarin release rate.

Embodiment 62: the method of embodiment 61, wherein the oil is derived from plant, animal or petrochemical sources.

Embodiment 63: the method of embodiment 61 or 62, wherein the oil is derived from a plant.

Embodiment 64: the method of any of embodiments 61-63, wherein the oil is derived from fruits, seeds or vegetables.

Embodiment 65: the method of any of embodiments 61-64, wherein the oil is derived from milk thistle fruits and/or seeds.

Embodiment 66: the method any of embodiments 61-65, wherein the release rate is improved by 1.0% or more.

Embodiment 67: the method of any of embodiments 61-66, wherein the release rate is improved by 5.0% or more.

Embodiment 68: the method of any of embodiments 61-67, wherein the release rate is improved by 10.0% or more.

Embodiment 69: the method of any of embodiments 61-68, wherein the release rate is improved by 20.0% or more.

Embodiment 70: disclosed herein is a dietary supplement composition containing the product of any of embodiments 1-31.

Embodiment 71: the dietary supplement composition of embodiment 70, wherein the dietary supplement composition is a tablet, dragee, capsule, pill, granule, solution, syrup, suspension or emulsion.

Embodiment 72: the dietary supplement composition of embodiment 70 or 71 for use in modifying liver function.

EXAMPLES

Example 1

The dissolution of silymarin isomers in milk thistle products was determined using a dissolution apparatus which conforms to Ph. Eur. and USP requirements. The dissolution apparatus has a conformation of paddles and the dissolution media is a buffer solution at pH 7.5 (degassed).

Extract 1 was prepared according to the steps below without adding the oil fraction of steps (a) and (b) in step (e). Extract 2 was prepared according to all steps (a) through (f) below:
  (a) providing an oily milk thistle extract obtained by degreasing the milk thistle fruit;
  (b) taking up the oily extract from (a) in an organic solvent to form a solution;
  (c) providing an additional extract from the degreased milk thistle fruit, wherein the additional extract is obtained by washing the degreased milk thistle fruit with a solvent and then subsequently removing said solvent;
  (d) taking up the additional extract from (c) in a solvent to form a solution;
  (e) combining the solution of (b), with the solution of (d) to form a combined extract solution, such that the amount of oily extract from (a) in the final product of (f) is 0.5-10.0% by weight;
  (f) removing the solvent of the combined extract solution of (e) to obtain a solid and optionally comminuting the solid wherein the product possesses a silymarin release rate is 90% or greater

| Sample | Dissolution Time | Dissolved Silymarin Quantity in % |
|---|---|---|
| Extract 1 | After 30 mins | >80.0% |
| Extract 2 | After 30 mins | >90.0% |

Example 2

Gas chromatography analysis of Extract 2 yielded a fatty acid content of 3.8% by weight. Gas chromatography analysis of Extract 1 yielded a fatty acid content of 1.0% by weight.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 3

Clinical Trial 1

Participants will be randomly assigned to receive silymarin or a vitamin supplement. Participants will be recruited from a cohort of hepatitis C infected individuals and will receive the supplements daily for 18 months, with measures obtained every six months. One tablet containing 210 mg of silymarin will be taken daily. Measures to be assessed will include: retention in the study, compliance with study assignment, self-described symptoms, alanine aminotransferase levels, serum collagen markers, abdominal ultrasound, viral load and clearance, and quality of life.

Clinical Trial 2

The study will be a double-blinded placebo controlled trial. We will compare a 4 week course of therapy with silymarin tablets containing 400 mg of Silymarin and a low-dose vitamin preparation (placebo) administered daily and then follow-up for a total of 8 weeks to assess treatment response. Outcomes of our randomized controlled trial are improvement in symptoms and signs, normalization of liver functions, time to resuming normal activities, and sense of well-being. Freshly collected serum will be tested for anti-HAV IgM, anti-HBc Igm, anti-HBs, HBs Ag, anti-HCV antibody, HCV-RNA, anti-HDV IgM, anti-HEV IgM, CMV and EBV and for alanine aminotransferase (ALT), AST, direct and total bilirubin.

Clinical Trial 3

This study will be an open label, randomized, dose-finding study. There will be three groups corresponding to three different IdB 1016 doses: 314 mg, 624 mg, and 942 mg tid. Each group will have 15 patients diagnosed with chronic hepatitis C and will be stratified to five patients with fibrosis stage II (periportal fibrosis), five patients with fibrosis stage III (bridging fibrosis), and five patients with fibrosis stage IV (compensated cirrhosis). The treatment duration will be 12 weeks. Patients will be followed for an additional 4 weeks after treatment cessation to assess residual effects of measured parameters. Patients will have clinic visits on Day-21

(screening), Day 1 (treatment initiation), Day 29, Day 57, Day 85 (end of treatment), and Day 113 (follow-up after washout).

What is claimed is:

1. A method for preparing a potent milk thistle extract, the method comprising:
   (a) cold pressing milk thistle fruit to yield (i) an oily milk thistle extract and (ii) a degreased milk thistle fruit;
   (b) adding the oily milk thistle extract from (a) to an organic solvent to form a first solution;
   (c) washing the degreased milk thistle fruit with a solvent and then subsequently removing the solvent to form an additional extract;
   (d) adding the additional extract from (c) to a solvent to form a second solution;
   (e) combining the first solution of (b), with the second solution of (d) to form a combined extract solution;
   (f) removing the solvent of the combined extract solution of (e) to obtain a solid and optionally comminuting the solid to form a potent milk thistle extract
   wherein the amount of the first solution of (b) added to the second solution (d) is such that the amount of oily milk thistle extract is 0.5-10.0% by weight of the potent milk thistle extract.

2. The method of claim 1, wherein the first solution of (b) is concentrated and/or filtered.

3. The method of claim 1, wherein the second solution of (d) is concentrated and/or filtered.

4. The method of claim 1, wherein the combined extract solution of (e) is concentrated and/or filtered.

5. The method of claim 1, wherein the additional extract of (c) is comminuted.

6. The method of claim 1, wherein the additional extract of (c) is re-solvated in an organic solvent, optionally concentrated and/or optionally filtered and dried and optionally comminuted prior to step (d).

7. The method of claim 1, wherein the organic solvent of (b) is an alcohol.

8. The method of claim 1, wherein the solvent of (c) is ethyl acetate, ethanol or methanol.

9. The method of claim 1, wherein the solvent of claim (d) is an alcohol.

10. The method of claim 1, wherein the amount of the first solution of (b) being added to the second solution (d) is such that the amount of oily milk thistle extract is 0.5-6.0% by weight of the potent milk thistle extract.

11. The method of claim 1, wherein the amount of the first solution of (b) being added to the second solution (d) is such that the amount of oily milk thistle extract is 1.0-3.0% by weight of the potent milk thistle extract.

12. A potent milk thistle extract comprising (a) 35%-70% by weight silymarin and (b) 0.5-10% by weight oily milk thistle extract, wherein the dissolution rate of the silymarin in the potent milk thistle extract is higher than the dissolution of silymarin in a similar composition without oil.

13. The potent milk thistle extract of claim 12, wherein (b) is 0.5-6.0% by weight oily milk thistle extract.

14. The potent milk thistle extract of claim 12, wherein (b) is 1-3% by weight oily milk thistle extract.

15. A method of treating diseases of the liver, the method comprising administering the potent milk thistle extract of claim 12 to a subject.

16. The method of claim 15, wherein the disease of the liver is selected from toxic liver damage, hepatoses, acute liver failure, liver necrosis, liver dystrophy, cirrhosis of the liver, hepatic fibrosis, hepatomegaly, fatty liver degeneration, liver insufficiency, and hepatitis.

17. The method of claim 15, wherein the disease of the liver is selected from fascioliasis, hepatitis, non-alcoholic steatohepatitis (NASH) with or without fibrosis, hepatic steatosis, fatty liver disease (FLD), non-alcoholic fatty liver disease (NAFLD), alcoholic liver disease, Alagille syndrome, biliary atresia, galactosemia, gallstones, hemochromatosis, liver cancer, lysosomal acid lipase deficiency (LALD), *porphyria*, acetaminophen hepatotoxicity, Reye's syndrome, sarcoidosis, tyrosinemia, Wilson disease, Gilbert's syndrome, cirrhosis, and primary sclerosing cholangitis.

18. The method of claim 15, wherein the disease of the liver is non-alcoholic fatty liver disease.

* * * * *